United States Patent [19]

Brodman et al.

[11] Patent Number: 5,002,540

[45] Date of Patent: Mar. 26, 1991

[54] INTRAVAGINAL DEVICE AND METHOD FOR DELIVERING A MEDICAMENT

[75] Inventors: Michael L. Brodman, Great Neck, N.Y.; Warren Kirschbaum, Kemah; Steven L. Weinberg, League City, both of Tex.

[73] Assignee: Warren Kirschbaum dba Medical Marketing Assoc., League City, Tex.

[21] Appl. No.: 355,407

[22] Filed: May 22, 1989

[51] Int. Cl.$^5$ .................. A61M 31/00; A61F 6/06
[52] U.S. Cl. .................. 604/285; 128/834; 604/55; 424/433; 424/457
[58] Field of Search .............. 128/830, 832, 833, 834; 604/890.1, 891.1, 48, 49, 54, 55, 285, 286; 424/430–433, 436, 438, 457

[56] References Cited

U.S. PATENT DOCUMENTS

| | | |
|---|---|---|
| 2,020,107 | 11/1935 | Cruickshank . |
| 3,545,439 | 12/1970 | Duncan . |
| 3,902,493 | 9/1975 | Baier et al. ............. 604/286 |
| 3,946,734 | 3/1976 | Dedrick et al. . |
| 3,975,350 | 8/1976 | Hudgin et al. . |
| 3,993,073 | 11/1976 | Zaffaroni ............. 128/833 |
| 3,995,633 | 12/1976 | Gougeon . |
| 4,160,452 | 7/1979 | Theeuwes ............. 424/431 |
| 4,177,256 | 12/1979 | Michaels et al. . |
| 4,198,965 | 4/1980 | Strickman et al. . |
| 4,203,440 | 5/1980 | Theeuwes . |
| 4,219,016 | 8/1980 | Drobish et al. . |
| 4,220,152 | 9/1980 | Dresback ............. 604/55 |
| 4,235,236 | 11/1980 | Theeuwes . |
| 4,286,587 | 9/1981 | Wong . |
| 4,309,996 | 1/1982 | Theeuwes . |
| 4,312,347 | 1/1982 | Magoon et al. ............. 128/260 |
| 4,327,725 | 5/1982 | Cortese et al. ............. 424/431 |
| 4,355,722 | 6/1982 | Jackson . |
| 4,369,773 | 1/1983 | Chvapil . |
| 4,381,780 | 5/1983 | Holloway ............. 424/438 |
| 4,455,144 | 6/1984 | Michaels . |
| 4,475,916 | 10/1984 | Himmelstein ............. 424/430 |
| 4,479,795 | 10/1984 | Mustacich et al. . |
| 4,526,578 | 7/1985 | Wong . |
| 4,578,075 | 3/1986 | Urquhart et al. . |
| 4,589,880 | 5/1986 | Dunn et al. . |
| 4,627,851 | 12/1986 | Wong et al. . |
| 4,629,449 | 12/1986 | Wong . |
| 4,699,823 | 10/1987 | Kellenberger et al. . |
| 4,786,500 | 11/1988 | Wong ............. 424/430 |
| 4,837,111 | 6/1989 | Deters et al. ............. 424/430 |
| 4,876,093 | 10/1989 | Theeuwes et al. ............. 424/438 |
| 4,915,949 | 4/1990 | Wong et al. ............. 424/438 |

OTHER PUBLICATIONS

Adamson, G. D., "Three-Day Treatment of Vulvovaginal Candidiasis," 158 Am J. Obstet. Gynecol. 1002 (1988).

LePage, Mary Ellen, et al., "Patient Acceptance of Prefilled Disposable Vaginal Applicator," 158 Am. J. Obstet. Gynecol. 1006 (1988).

*Primary Examiner*—C. Fred Rosenbaum
*Assistant Examiner*—Sharon Rose
*Attorney, Agent, or Firm*—Vaden, Eickenroht, Thompson & Boulware

[57] ABSTRACT

A device for inserting into the vagina of a patient for delivery of a medicament in the vagina. The walls of the tubular member comprising the device are comprised of water-swellable materials having a higher porosity at one end than the other, the relatively low porosity end being positioned distally in the vagina to the relatively high porosity end. The medicament is contained within a reservoir in the tubular member and delivered to the vagina through the pores in the walls of the tubular member at different rates depending upon the porosity. Also provided is a method of delivering a medicament to the vagina of a patient.

14 Claims, 1 Drawing Sheet

FIG.1
FIG.2
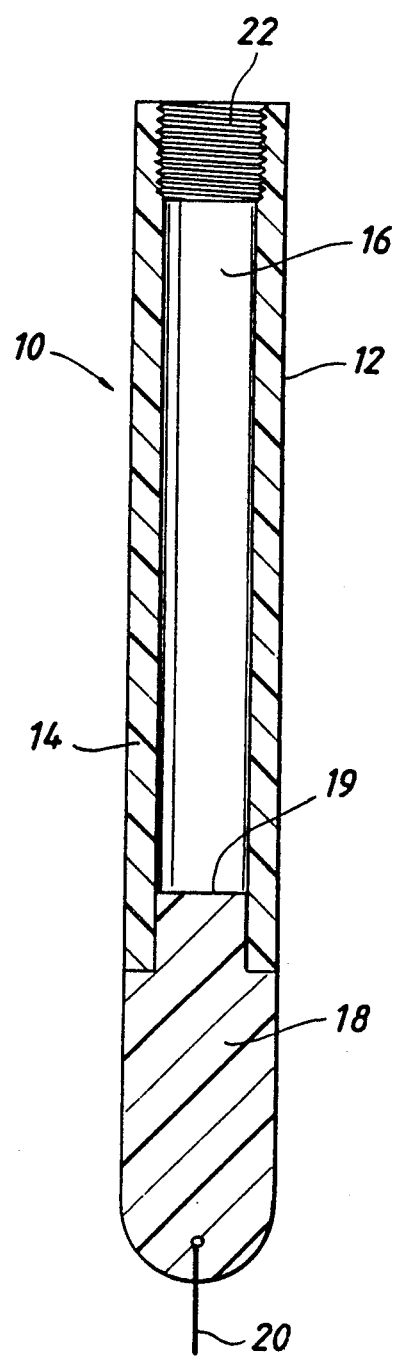
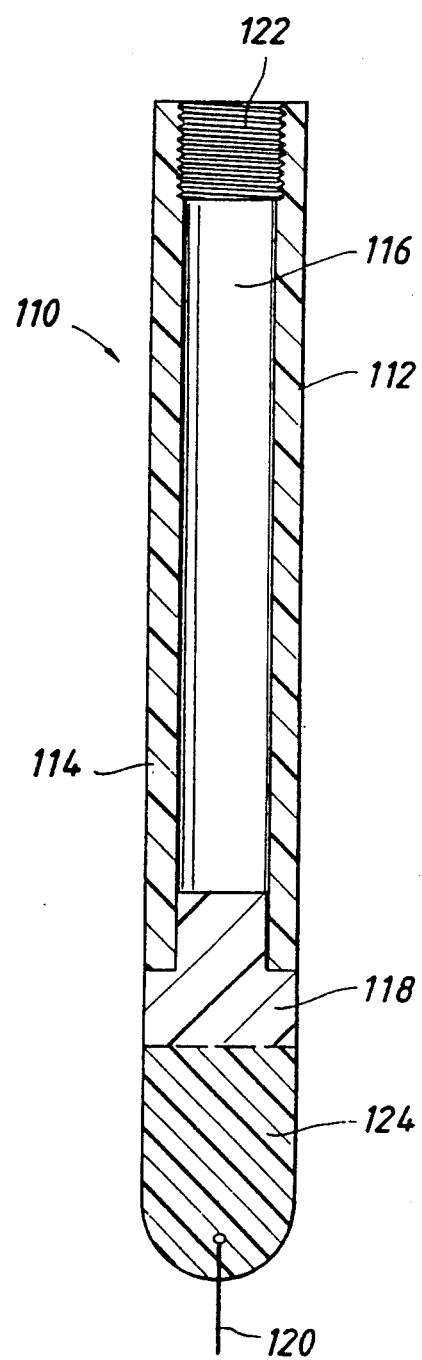

INTRAVAGINAL DEVICE AND METHOD FOR DELIVERING A MEDICAMENT

BACKGROUND OF THE INVENTION

The present invention relates to a device and method for delivering a medicament within the vagina of a patient. More particularly, the present invention relates to an intravaginal device for delivery of a medicament to the patient, the intravaginal device having a central reservoir for containing the medicament, the walls of the reservoir being comprised of a material having varying porosity depending upon whether it is desired to deliver the medicament to the vagina, prevent the delivery of the medicament, or absorb the medicament if it is desired to, for instance, limit the time or control the location to which the medicament is delivered in the vagina.

Many monolithic systems and devices for delivery of a medicament are known in the art, as are monolithic devices for delivery of the medicament or other beneficial agent in the vagina. For instance, the following U.S. Pat. Nos. disclose various devices designed to be placed in the vagina for dispensing a spermicide at a controlled, spermicidally effective release rate:

| | | |
|---|---|---|
| 2,020,107 | Cruickshank | 11/05/35 |
| 4,198,965 | Strickman, et al. | 04/22/80 |
| 4,219,016 | Drobish, et al. | 08/26/80 |
| 4,369,773 | Chvapil | 01/25/83 |
| 4,526,578 | Wong | 07/02/85 |
| 4,589,880 | Dunn, et al. | 05/20/86 |

Also known are several U.S. Pat. Nos. describing intravaginal devices for dispensing drugs or hormones. These patents include:

| | | |
|---|---|---|
| 3,545,439 | Duncan | 12/08/70 |
| 3,995,633 | Gougeon | 12/07/76 |
| 4,286,587 | Wong | 09/01/81 |
| 4,312,347 | Magoon, et al. | 01/26/82 |
| 4,629,449 | Wong | 12/16/86 |

These patents all describe devices which comprise a reservoir formed by a polymeric material which is permeable to the drug or hormone contained within the reservoir, the device itself being shaped to be retained within the vagina. U.S. Pat. No. 3,975,350, assigned to Princeton Polymer Laboratories, Incorporated is directed to the polymeric material itself.

Many U.S. Pat. Nos. describe devices comprised of polymeric materials for ingestion or placement in a body cavity, and a sample of such patents includes the following:

| | | |
|---|---|---|
| 3,946,734 | Dedrick, et al. | 03/30/76 |
| 4,203,440 | Theeuwes | 05/20/80 |
| 4,235,236 | Theeuwes | 11/25/80 |
| 4,309,996 | Theeuwes | 01/12/82 |
| 4,455,144 | Michaels | 01/19/84 |
| 4,578,075 | Urquhart, et al. | 03/25/86 |
| 4,627,851 | Wong, et al. | 12/09/86 |

This last group of U.S. Pat. Nos. is listed here not because they are representative of references describing such devices but because the devices they describe are all more or less tubular in shape and include a central reservoir, the walls of the reservoir being comprised of the polymeric material. As will be seen, two of the structural features of the apparatus of the present invention can be characterized in this same manner.

The Theeuwes '440 patent is of particular interest because that patent describes a tubular device which includes a reservoir, or chambers, for containing a supply of a drug, hormone, or other beneficial agent which is dispensed from one end of the device. The drug is said to be dispensed under the influence of a pressure generating member which swells when the device is placed in a fluid environment to apply pressure against the chamber, thereby decreasing the volume of the chamber to dispense the drug. The chamber is said to be formed of an elastomeric, low modulus material which collapses in response to applied pressure.

In spite of these numerous prior patents, representing several attempts to solve the problem of efficacious delivery of a medicament to a patient, and specifically, to the vagina of the patient, there are still applications in which there is a need for an improved intravaginal device for delivery of a medicament, and a method of delivering a medicament, to a patient. For instance, even though devices such as those described in the above-listed patents are known, the prescriptions for almost all medicaments prescribed for intravaginal administration by the patient recite that the medicament should be taken before bed. The reason for that recitation is that the patient is supine when sleeping; consequently, the medicament is less likely to flow out of the vagina under the influence of gravity because the patient is not erect. A device which is capable of effectively delivering a medicament to the patient regardless of whether the patient is supine or erect not only eliminates the requirement that the medicament be administered before bed, but also makes possible the administration of the medicament around the clock. It is, therefore, an object of the present invention to provide such a device and such a method.

Another example of the need for an improved method and device for delivering a medicament in the vagina is provided by reference to the generally accepted methods for treatment of a patient with caustic medicaments such as 5-fluorouracil (5-FU). This commonly used anti-neoplastic agent, and other topically-applied medicaments, can damage the skin upon prolonged contact. Consequently, when indicated for vaginal neoplasia, 5-FU is administered by the physician, either as a cream or in propylene glycol solution, while the patient is supine so as to prevent the leaching of 5-FU out of the vagina onto the skin of the vulvular region. A device which prevents the leaching of such caustic medicaments out of the vagina would eliminate the requirement of an office or clinical visit by the patient, eliminate the possibility of damage to the skin, and make it possible to administer the medicament continuously, if desired, rather than only during the office or clinical visit, thereby increasing the efficacy of the medicament. It is, therefore, another object of the present invention to provide such a method and such a device.

It is another object of the present invention to provide a method and device capable of delivering a medicament to the vagina at a relatively constant, therapeutically effective dosage level.

Another object of the present invention is to provide a method and device for retaining a medicament within the vagina once the medicament has been delivered to the vagina.

It is another object of the present invention to provide a device having a reservoir therein for containing a sufficient quantity of a medicament to be delivered therefrom so as not to require frequent removal of the device for replenishment of the medicament.

It is another object of the present invention to provide a device and a method for topical application of a medicament to the vaginal mucosa.

These and other objects of the present invention will be apparent to those skilled in the art from the following description of a preferred embodiment thereof

SUMMARY OF THE INVENTION

These objects, and the advantages of the present invention, are achieved by providing an intravaginal device for delivery of a medicament comprising a generally elongate, tubular member comprised of a waterswellable, porous material, the length and diameter of the tubular member being selected so as to ensure engagement of the walls of the vagina and retention therein upon swelling of the tubular member when inserted into the vagina of a patient. The tubular member is provided with means for closing the end thereof to form a reservoir for receipt of a medicament therein. The porosity of the material comprising the tubular member is selectively varied along the length of the tubular member in accordance with whether the medicament within said tubular member is to be delivered to the vagina from the reservoir, retained within the reservoir, or delivered to the vagina from the reservoir and then absorbed by the tubular member.

Also provided is a method of dispensing a medicament in the vagina of a patient from a device placed in the vagina comprising filling the reservoir of a generally elongate, tubular member with a medicament to be delivered to a patient from within the vagina of the patient and then inserting the tubular member into the vagina. The tubular member is comprised of a waterswellable, porous material which, upon contact with the aqueous environment of the vagina, swells to engage the vaginal mucosa, thereby ensuring the retention of the device within the patient's vagina. The medicament is dispensed from the device through the porous walls thereof, the porosity of the material being selectively varied along the length thereof, for dispensing the medicament at different rates along the length of the tubular member.

BRIEF DESCRIPTION OF THE DRAWINGS

FIG. 1 is a longitudinal, sectional view of a preferred embodiment of a device constructed in accordance with the teachings of the present invention.

FIG. 2 is a longitudinal, sectional view of a second preferred embodiment of a device constructed in accordance with the teachings of the present invention.

DETAILED DESCRIPTION OF THE PREFERRED EMBODIMENTS

The term "medicament" as used herein refers to any pharmacological agent which can be advantageously delivered in the vagina and which is capable of being delivered to the vagina from a central reservoir by passing through the walls of the device comprising the reservoir. The medicament need not be an agent which exerts a therapeutic effect on the vagina; it is envisioned that agents which exert their effect elsewhere on the patient's body, e.g., medicaments capable of systemic effects, may also be appropriate for use in connection with the method and device of the present invention. The preferred medicaments for use in connection with the present invention can be grouped into four general classes as follows:

| CLASS NO. | CLASS TYPE | EXAMPLES |
|---|---|---|
| I | antifungal/antibacterial agents | clotrimazole, miconazole nitrate, aminacrine hydrochloride, Gentian violet, iodoquinol (diiodohydroxyquin), clioquinol (iodochlorohydroxyquin), acetic acid, sulfisoxazole and other sulfonamides, nystatin |
| II | anti-protozoan agents | furazolidine, metronidazole, iodoquinol (diiodohydroxyquin) |
| III | chemotherapeutics | 5-fluorouracil |
| IV | anti-inflammatory/ non-specific infectious agents | diethylstilbestrol, hydrocortisone, cortisol, buffered acid vaginal jelly, pregnidisone |

These four preferred classes of medicaments which are appropriate for use in connection with the device and method of the present invention are set out for purposes of illustration and not by way of limitation. Other agents may be appropriate medicaments for use in connection with the present invention. For instance, a therapeutic agent such as interferon, digitoxin, triiodothyronine, isoproterenol, atropine, histamine, nitrogen mustard, vitamin $B_{12}$, pyrimethamine, or hormones such as estradiol, progesterone, androstenedione, testosterone, medroxyprogesterone acetate, melengestrol acetate, chlormadinone, anti-fertitily steroids, and other agents known from such commonly utilized authorities as Remington's Pharmaceutical Sciences (Mack Easton Publishing Co., Easton, Pa.) and Goodman and Gilman, The Pharmacological Basis of Therapeutics (MacMillian Company, London) may also be advantageously administered by delivery in the vagina, and any other therapeutic agent which can be formulated in aqueous solution and absorbed through the vaginal mucosa can be delivered in a device constructed in accordance with the present invention. Those medicaments which are not soluble in water can also be used if capable of passage through the walls of the device, as will be described. In addition, many medicaments which are capable of only limited solubility in water are appropriate for use in connection with the device and method of the present invention when prepared in aqueous solution of the medicament in the form of pharmacologically acceptable salts such as hydrochlorides, hydrobromides, sulfate, laurylate, palmitate, phosphate, nitrate, borate, acetate, maleate, tartrate, oleates and salicylate. The device and method of the present invention are particularly useful for patients requiring topical application of a medicament to the mucosa of the vagina, and for that reason, anti-fungal, antibacterial, and anti-protozoan agents are preferred medicaments for use in connection with the device and method of the present invention.

The phrase "water swellable, porous material" refers to a material which, when placed in an aqueous environment such as the normal vaginal secretions of the patient, swells, or increases in volume. Such materials are characterized as being highly porous, even in the "unswollen" state, to solutions such as aqueous solutions of a medicament contained within the reservoir of the device of the present invention. Appropriate water-swellable, porous materials for use in constructing the device of the present invention include cross-linked hydrophilic materials such as hydrogels and include polyhydroxyalkylmethacrylates, polyacrylamide, polymethylamide, poly(N-vinyl-2-pyrrolidone), copolymers of styrene, ethylene, propylene, butylene, or isobutylene with maleic or fumaric anhydride, polyvinyl alcohol, hydroxylated polyvinyl acetal, collagen, and polyurethane. The presently preferred water-swellable, porous materials for use in connection with the device of the present invention are polyvinyl alcohol, hydroxylated polyvinyl acetal, collagen, and polyurethane.

Referring now to FIG. 1, there is shown a presently preferred embodiment of the device of the present invention, indicated generally at reference numeral 10. The device 10 is comprised of a generally elongate, tubular member 12, the walls of which are comprised of the water-swellable, porous material characterized above. As used herein, the term "walls" refers collectively to side walls 14 and the means for closing one end of member 12 described below. The length and diameter of member 12 are selected so as to ensure engagement of the mucosa of the walls of the vagina, and retention therein, when in the swollen condition resulting from the placement of the device 10 into an aqueous environment such as the normally moist condition of the vagina resulting from the secretions of the vaginal mucosa.

The device 10 is provided with means for closing one end of tubular member 12 to form a reservoir 16 within member 12 which may take the form of the cap 18 having a string 20 mounted therein to facilitate retrieval of the device 10 from the vagina. Cap 18 is secured to tubular member 12 by a suitable solvent or adhesive depending upon the nature of the material comprising cap 18 and tubular member 12, or by mechanical means such as by sizing the diameter of the portion of cap 18 which is inserted into tubular member 12 slightly larger than the inside diameter of reservoir 16. In the case of materials such as the polyvinyl alcohols and hydroxylated polyvinyl acetals, an adhesive of a type known in the art which infiltrates the pores of those materials and then hardens to form a matrix which holds the cap 18 and tubular member 12 together is preferred. If cap 18 and tubular member 12 are comprised of polyurethanes, an isocyanate will accomplish the bonding. Although shown as cap 18, the phrase "means for closing one end of member 12" is used in connection with the description of the device 10 throughout this specification because those skilled in the art who have the benefit of this disclosure will recognize that the end of member 12 could also be closed by a semi-porous membrane or a plug, or that the walls of the entire tubular member 12 could be constructed of a single water-swellable material molded as a single piece to form the cap 18 integrally with the side walls 14.

The inside of the side walls 14 of member 12 is provided with means adapted for engaging the dispenser in which the medicament is supplied (not shown) to facilitate transfer of the medicament out of another container into the reservoir 16. In a presently preferred embodiment, the dispenser engaging means comprises a set of screw threads 22 at the end of tubular member 12 opposite cap 18 for receiving the threads of the vial or ampule (not shown) in which the medicament is supplied. Those skilled the art who have the benefit of this disclosure will recognize that the dispenser engaging means may also take the form of an apparatus such as a LEUR-LOK device for convenient connection to a larger reservoir containing the medicament, a cap of NEOPRENE, latex, cellulosic, or other suitable material through which the stylet of a syringe is inserted for dispensing medicament into the reservoir 16 under sterile or semi-sterile conditions, or a nipple for receiving the spout of a tube or other container out of which the medicament is poured or squeezed. All such containers in which a medicament can be supplied are collectively referred to herein as "dispensers", hence the use of the phrase "dispenser engaging means" in connection with the description of the threads 22.

When the device 10 is inserted into the vagina of a patient, the end of tubular member 12 which is closed by cap 18 is positioned distally, e.g., in the lower vagina, and the other end, e.g., the end which is provided with the means for engaging the dispenser such as the threads 22, is positioned proximally in the upper vagina. The two-piece construction described above, e.g., tubular member 12 and cap 18, facilitates the selective variation of the porosity of the waterswellable, porous material comprising the side walls 14 of tubular member 12 in accordance with whether the medicament contained within reservoir 16 is to be delivered to the vagina from the reservoir 16, retained within the reservoir 16, or delivered to the vagina from the reservoir 16 and then absorbed by a portion of the tubular member 12. By way of example, and not limitation, in the device shown at reference numeral 10, the side walls 14 of tubular member 12 are comprised of a water-swellable, relatively porous material having a porosity ranging from about 60 to about 85% such as polyvinyl alcohol, collagen or polyurethane, and the cap 18 is comprised of a water-swellable, relatively nonporous material. The relatively non-porous cap 18 either prevents delivery of the medicament from reservoir 16 or delivers the medicament at a slower rate than the rate at which the medicament is delivered through the side walls 14 of tubular member 12. Suitable caps for use in connection with the device 10 are those comprised of a water-swellable material having a porosity range of from about 0 up to about 60% such as polyvinyl alcohol, collagen, or polyurethane. When the porosity of cap 18 approaches zero, the cap 18 effectively functions as a plug such that the medicament dispensed through the side walls 14 of tubular member 12 is retained within the vagina when the swollen cap engages the vaginal mucosa. Although some absorption of the medicament occurs, such low porosity caps also prevent the passage of the medicament out of reservoir 16 through the cap, effectively causing the medicament to be retained in member 12 over that portion of the walls thereof. To prevent absorption of the medicament into cap 18 through the center of tubular member 12, a barrier 19 may be secured between cap 18 and the side walls 14 of tubular member 12 or placed, in the case of tubular member 112, at the distal end of reservoir 116 inside of plug 118 as will be described. Barrier 19 is preferably comprised of a non-porous sealer such as polyurethane or silicone, latex or other rubber, or a heat-sealed section of cap 18.

As noted above, the walls of tubular member 12 (e.g., side walls 14 and cap 18) may also be integral, and in that embodiment, the porosity of the walls is varied continuously from one relatively porous end for positioning in the upper vagina to the other, closed, relatively non-porous end of tubular member 12 which is positioned in the lower vagina. In this embodiment (not shown), as in the case of the device 10, the medicament contained within reservoir 16 is dispensed from the relatively porous end of the tubular member 12 and retained within the vagina by the relatively non-porous end. In a presently preferred embodiment, such a device is comprised of polyvinyl alcohol having a porosity ranging from about 60 to about 85% at the relatively porous end down to from about 0 to about 60% at the relatively non-porous, closed end.

Another preferred embodiment of a device constructed in accordance with the present invention is shown in FIG. 2. That device, indicated generally at reference numeral 110, is also comprised of an elongate tubular member 112 and a means for closing one end of tubular member 112. In the case of the device 110, the closing means takes the form of a plug 118 which is secured to the side walls 114 of tubular member 112, thereby forming the reservoir 116 within tubular member 112. The side walls 114 of tubular member 112 are comprised of a relatively porous, water-swellable material, e.g., having a porosity ranging from about 60 to about 85%, for delivering the medicament within the reservoir 116 of the vagina. Plug 118 is comprised of a relatively non-porous, water-swellable material, preferably a material having a porosity ranging from about 0 to about 15%, and is provided with a high porosity, absorbent section 124. The porosity of section 124 preferably ranges from about 40 to about 85% such that medicament which is delivered to the vagina through the walls of tubular member 112, and which is not retained within the vagina above plug 118, is absorbed when the medicament reaches that portion of the lower vagina in which section 124 is positioned. Section is secured to plug 118 as described above, and is provided with a string 120 to facilitate removal of the device 110 from the vagina.

The structure of device 110 provides two advantages which, on information and belief have not heretofore been obtainable. In particular, the dosage of the medicament delivered from reservoir 116 to the vagina is controlled because absorbent section 114 effectively acts as a sponge to slowly draw the medicament delivered from reservoir 116 past plug 118 by absorbing any medicament in the vagina below plug 118. This absorbent action by section decreases the likelihood of an accumulation of a large amount of the medicament above plug 118 and a resultant exposure to too much of the medicament thereby providing a means for delivering the medicament to the vagina at a relatively constant, therapeutically effective dosage level. In this same manner, the structure of the device 110 provides the opportunity for application of the medicament to the mucosa at a particular location in the vagina, an advantage in therapy of certain types of vaginal disorders. For instance, the efficacy of therapy for genital warts (condyla) can be enhanced by, or may even be dependent upon, the topical application of a medicament such as 5-fluorouracil to the affected area. In the event of an eruption in the vaginal mucosa, a device such as the device 110 is prepared having a tubular member of a length selected so that plug 118 is positioned just below the eruption, causing the medicament to "pool" at the level of the eruption with a fresh, constant supply of medicament being pooled by the slow drawing of the medicament past plug 118 by section.

It will be understood by those skilled in the art who have the benefit of this disclosure that plug 118 and section can be integral, e.g., can be molded from a water-swellable material having a porosity which continuously varies from the portion of plug 118 which closes tubular member 112 down to the tip of section 124 in which string 120 is mounted in the same manner as described above in connection with an tubular member 12 and cap 18. The range of porosity of such an integral structure is from about 0 to from about 40 at the end which closes tubular member 112 up to about 85% at the end in which string 120 is mounted. It will likewise be understood that various combinations of tubular members having a porosity which is continuously varied, tubular members having the same porosity along the side walls thereof, end closing means, absorbent sections, and integral end closing means and absorbent sections can be assembled to achieve a treatment regimen in accordance with the method of the present invention which is beneficial to a particular patient. The design of these various combinations for achieving a particular treatment regimen can be better understood by reference to the following examples of the method of delivering a medicament from the reservoir of the device to be placed in the vagina of a patient.

Example 1

A device was constructed in accordance with the teachings of the present invention, the walls of which were comprised of hydroxylated polyvinyl acetal (Americal) having varying porosities. The reservoir was filled with the antifungal/antibacterial agent MONOSTAT (Ortho) in the formulation in which that medicament is supplied commercially and the device was then inserted into a moistened towel used to simulate the vaginal mucosa. After approximately 4 to 5 minutes, the towel was removed from the device and observed. The amount of medicament observed on the towel was greater at the proximal end of the device, indicating that the medicament was dispensed from the reservoir at a higher rate through the side walls of the tubular member than through the cap closing the distal end of the tubular member. It appeared that no medicament was dispensed from the cap.

Example 2

An experiment was conducted with the hydroxylated polyvinyl acetal used for the side walls of the tubular member of Example 1 to assess the water uptake, and hence, the relative porosity, of those materials. A 0.966 $in^3$ section of hydroxylated polyvinyl acetal of the type used for constructing the proximal portion of the walls of the device was weighed dry and was then fully hydrated and weighed. The net increase in weight showed a water uptake of 70.3%. When using a 1.125 $in^3$ piece of the hydroxylated polyvinyl acetal comprising the distal portion of the walls of the device, the water uptake was 57%. These results indicate that variation in the porosity of the walls of the device was achieved.

Although the invention has been described in terms of the above-illustrated preferred embodiments and the above-summarized examples, it will be understood by those skilled in the art who have the benefit of this disclosure that changes can be made to those embodiments and methods without departing from the spirit of the present invention, the descriptions being illustrative rather than a complete list of all possible embodiments and methods. Such changes are intended to fall within the scope of the following claims.

What is claimed:

1. An intravaginal device for delivery of a medicament comprising:
    an elongate, tubular member comprised of a water-swellable, porous material, the length and diameter of said tubular member being selected so as to ensure engagement of the walls of the vagina and retention therein upon swelling of said tubular member when said tubular member is inserted into the vagina of a patient;
    means for closing one end of said tubular member to form a reservoir within said tubular member for receipt of a medicament to be delivered within the vagina of a patient; and
    the porosity of the water-swellable, porous material comprising the walls of said tubular member being selectively varied along the length thereof in accordance with whether the medicament within said tubular member is to be delivered to the vagina from the reservoir, retained within the reservoir, or delivered to the vagina from the reservoir and then absorbed by said tubular member.

2. The device of claim 1 wherein the walls of one end of said tubular member are relatively porous for delivering the medicament to the vagina and the other end is relatively non-porous for preventing delivery of the medicament from the reservoir, the relatively non-porous end of said tubular member functioning to retain the medicament within the vagina when positioned in the lower vagina and the other end is positioned in the upper vagina.

3. The device of claim 2 wherein the porosity of the walls of the relatively porous end of said tubular member ranges from about 60 to about 85% and the porosity of the walls of the relatively non-porous end of said tubular member ranges from about 0 to about 60%.

4. The device of claim 2 additionally comprising an absorbent extension of the non-porous end of said tubular member.

5. The device of claim 1 wherein the porosity of the walls of said tubular member is varied continuously from one relatively porous end for positioning in the upper vagina to the other relatively non-porous end for positioning in the lower vagina whereby the medicament contained within the reservoir is dispensed from the porous end of said tubular member and retained within the vagina by the non-porous end of said tubular member.

6. The device of claim 5 additionally comprising an absorbent extension of the non-porous end of said tubular member.

7. A method of dispensing a medicament in the vagina of a patient from a device placed in the vagina comprising:
    filling a reservoir formed by the walls of a generally elongated, tubular member with a medicament to be delivered to a patient from within the vagina of the patient;
    inserting the tubular member into the vagina; and
    dispensing the medicament from the reservoir through the walls thereof at different rates along the length of the tubular member, the rate at which the medicament is dispensed being a function of the porosity of the material comprising walls of the medicament is dispensed being a function of the porosity of the material comprising walls of the tubular member, which porosity is varied along the length of the tubular member.

8. The method of claim 7 wherein the medicament is dispensed through the walls at the end of the tubular member positioned in the upper vagina at a rate which is higher then the rate at which the medicament is dispensed through the walls at the end of the tubular member which is positioned in the lower vagina.

9. The method of claim 8 additionally comprising absorbing the medicament in the lower vagina.

10. An intravaginal device for delivery of a medicament comprising:
    an elongate tubular member comprised of a waterswellable porous material, the length and diameter of said tubular member being selected so as to insure engagement of the walls of the vagina and retention therein upon swelling of said tubular member when said tubular member is inserted into the vagina of a patient;
    means for closing one end of said tubular member to form a reservoir within said tubular member for receipt of a medicament to be delivered within the vagina of a patient; and
    the porosity of the water-swellable, porous material comprising the walls of said tubular member being varied along the length thereof, the walls of said tubular member being relative porous for delivering the medicament to the vagina at one end and relatively non-porous for preventing delivery of medicament from the reservoir to the vagina at the other end, the relatively non-porous end of said tubular member functioning to retain the medicament within the vagina when positioned in the lower vagina and the other end is positioned in the upper vagina.

11. The device of claim 10 wherein the porosity of the walls of the relatively porous end of said tubular member ranges from about 60 to about 85% and the porosity of the walls of the relatively non-porous end of said tubular member ranges from about 0 to about 60%

12. The device of claim 11 additionally comprising an absorbent extension of the non-porous end of said tubular member.

13. The device of claim 10 wherein the porosity of the walls of said tubular member is varied continuously from the relatively porous end to the relatively non-porous end.

14. The device of claim 13 additionally comprising an absorbent extension of the non-porous end of said tubular member for drawing the medicament dispensed through the walls of said tubular member from the relatively porous end past the non-porous end by absorbing the medicament in the lower vagina in which said absorbent extension is positioned.

* * * * *